(12) United States Patent
Bapat et al.

(10) Patent No.: US 8,071,767 B2
(45) Date of Patent: Dec. 6, 2011

(54) PROCESS FOR PREPARATION OF 9-HYDROXY-3-(2-CHLOROETHYL)-2-METHYL-4H-PYRIDO[1,2-A]PYRIMIDIN-4-ONE HYDROCHLORIDE

(75) Inventors: Uday Rajaram Bapat, Mumbai (IN); Munusamy Jayamani, Chennai (IN); Sivaji Ravisaravanan, Madurai (IN); Vigneshwara Ravisankar, Tirunelveli (IN)

(73) Assignee: Actavis Group PTC EHF (IS)

( * ) Notice: Subject to any disclaimer, the term of this patent is extended or adjusted under 35 U.S.C. 154(b) by 274 days.

(21) Appl. No.: 12/522,282

(22) PCT Filed: Jan. 8, 2008

(86) PCT No.: PCT/IB2008/000626
§ 371 (c)(1),
(2), (4) Date: Jul. 7, 2009

(87) PCT Pub. No.: WO2008/087557
PCT Pub. Date: Jul. 24, 2008

(65) Prior Publication Data
US 2010/0004447 A1    Jan. 7, 2010

(30) Foreign Application Priority Data
Jan. 8, 2007   (IN) .............................. 41/CHE/2007

(51) Int. Cl.
*C07D 239/70* (2006.01)
(52) U.S. Cl. ........................................................ 544/282
(58) Field of Classification Search .................. None
See application file for complete search history.

(56) References Cited

U.S. PATENT DOCUMENTS

| 4,804,663 A | 2/1989 | Kennis et al. |
| 5,158,952 A | 10/1992 | Janssen et al. |
| 5,254,556 A | 10/1993 | Janssen et al. |
| 5,688,799 A | 11/1997 | Vandenberk et al. |

FOREIGN PATENT DOCUMENTS

| EP | 0368388 A2 | 10/1989 |
| WO | 9514691 | 6/1995 |
| WO | WO/9623784 | * 8/1996 |
| WO | 2006027370 A1 | 3/2006 |

OTHER PUBLICATIONS

Kennis, et. al., Bioorganic & Medicinal Chemistry Letters (2000), 10(1), 71-74.*
International Search Report and Written Opinion; International Application No. PCT/IB2008/000626; International Filing Date Jan. 8, 2008; Date of Mailing: Dec. 18, 2008; 16 pages.
DeSMET, et al.; "Selectivity Control by Use of Near-IR for a Hydrogenation Process"; Organic Process Research & Development; 9; pp. 344-347; (2005).
Badawey, et. al.; "Synthesis of Some New Imidazo[1,2-a]pyrimidin-5(1H)-ones as Potential Antineoplastic Agents"; Journal of Heterocyclic Chemistry; 32; pp. 1003-1006; (1995).

* cited by examiner

*Primary Examiner* — Jeffrey Murray
(74) *Attorney, Agent, or Firm* — Cantor Colburn LLP

(57) ABSTRACT

Described herein is an improved, commercially viable and industrially advantageous process for the preparation of paliperidone intermediate 9-hydroxy-3-(2-chloroethyl)-2-methyl-4h-pyrido[1,2-a]pyrimidin-4-one and its hydrochloride salt. The process provides the paliperidone intermediate in higher yield and reduced reaction time compared to the previously disclosed processes, thereby providing for production of paliperidone and its pharmaceutically acceptable acid addition salts in high purity and in high yield.

13 Claims, No Drawings

PROCESS FOR PREPARATION OF 9-HYDROXY-3-(2-CHLOROETHYL)-2-METHYL-4H-PYRIDO[1,2-A]PYRIMIDIN-4-ONE HYDROCHLORIDE

CROSS-REFERENCE TO RELATED APPLICATIONS

This application is a 371 of PCT/IB2008/000626 filed Jan. 8, 2008, which claims the benefit of the filing date of Jan. 8, 2007 to Indian Application No. 41/CHE/2007 under provisions of 35 U.S.C. 119 and the International Convention for the protection of Industrial Property.

FIELD OF THE DISCLOSURE

Described herein is an improved, commercially viable and industrially advantageous process for the preparation of paliperidone intermediate, 9-hydroxy-3-(2-chloroethyl)-2-methyl-4H-pyrido[1,2-a]pyrimidin-4-one and its hydrochloride salt.

BACKGROUND

U.S. Pat. Nos. 4,804,663 and 5,158,952 disclose a variety of 3-piperidinyl-1,2-benzisoxazole derivatives, processes for their preparation, pharmaceutical compositions comprising the derivatives, and methods of use thereof. These compounds have long-acting antipsychotic properties and are useful in the treatment of warm-blooded animals suffering from psychotic diseases. Among them, paliperidone, (±)-3-[2-[4-(6-fluoro-1,2-benzisoxazol-3-yl)-1-piperidinyl]ethyl]-6, 7,8,9-tetrahydro-9-hydroxy-2-methyl-4H-pyrido [1,2-a] pyrimidin-4-one, is an antipsychotic agent and indicated for the both acute (short-term) and maintenance (long-term) treatment of schizophrenia. Paliperidone is represented by the following structural formula:

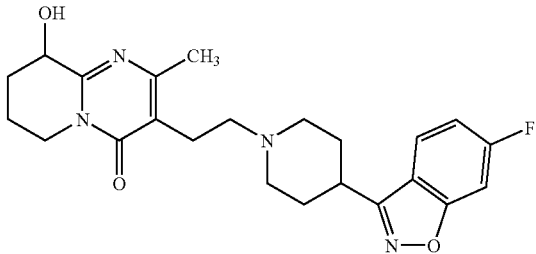

Processes for the preparation of paliperidone and related compounds are disclosed in U.S. Pat. Nos. 5,158,952, 5,254,556 and 5,688,799.

In the preparation of paliperidone, 9-hydroxy-3-(2-chloroethyl)-2-methyl-4H-pyrido[1,2-a]pyrimidin-4-one of formula I:

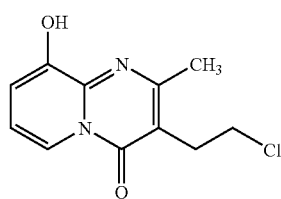

I is a key intermediate. According to U.S. Pat. Nos. 5,158,952 (hereinafter referred to as the '952 patent) and 5,254,556 (hereinafter referred to as the '556 patent), the compound of formula I can be prepared by the reaction of an optionally protected 2-aminopyridine compound with an α-acyl lactone compound in the presence of an activating reagent and in a suitable reaction-inert solvent such as toluene at a temperature 90° C. followed by treatment with ammonium hydroxide. The activating reagents include halogenating reagents such as, for example, phosphoryl chloride, phosphoryl bromide, phosphorous trichloride, thionyl chloride, and preferably phosphoryl chloride. The reaction mass is extracted with the solvents such as trichloromethane and then subjected to column chromatographic purifications.

The compound of formula I obtained by the process described in the '952 and the '556 patents is generally not of satisfactory purity. Unacceptable amounts of impurities are generally formed during the reaction between the 2-aminopyridine compound and the α-acyl lactone compound when the reaction is carried out in the presence of solvents like toluene, thus resulting in a poor product yield. In addition, the reaction proceeds at higher temperatures, and the process involves the additional step of column chromatographic purifications. Methods involving column chromatographic purifications are generally undesirable for large-scale operations, thereby making the process commercially unfeasible.

According to the U.S. Pat. No. 5,688,799 (hereinafter referred to as the '799 patent), the compound of formula I is prepared by the reaction of 2-amino-3-hydroxypyridine with 2-acetylbutyrolactone in the presence of p-toluenesulfonic acid in xylene solvent at reflux temperature for overnight using a water separator to yield 9-hydroxy-3-(2-hydroxyethyl)-2-methyl-4H-pyrido[1,2-a]pyrimidin-4-one. The 9-hydroxy-3-(2-hydroxyethyl)-2-methyl-4H-pyrido[1,2-a] pyrimidin-4-one is converted into its hydrochloride salt, followed by reaction with thionyl chloride in dimethylformamide to produce 9-hydroxy-3-(2-chloroethyl)-2-methyl-4H-pyrido[1,2-a]pyrimidin-4-one.

The synthetic route for the compound of formula I as described in the '799 patent involves a lengthy process, the yields obtained in this process are very low, and also the process produces a product of unsatisfactory purity. This process is also commercially unfeasible. Moreover, the intermediate compound 9-hydroxy-3-(2-hydroxyethyl)-2-methyl-4H-pyrido[1,2-a]pyrimidin-4-one obtained in this process is poorly soluble in xylene, resulting in deposit formation on the wall of the reaction vessel and discoloration of the reaction mixture to black. Furthermore, the reaction with thionyl chloride is characterized by a very severe smell, likely caused by reaction of residual 2-acetylbutyrolactone remaining from the previous step. The process generally results in a product of unreproducible yield and quality.

PCT Publication No. WO 2006/027370 describes a modified process for preparation of 9-hydroxy-3-(2-hydroxyethyl)-2-methyl-4H-pyrido[1,2-a]pyrimidin-4-one involving the reaction of 2-amino-3-hydroxypyridine with 2-acetylbutyrolactone in the presence of p-toluenesulfonic acid and using chlorobenzene as a solvent at reflux temperature, i.e., at 125° C. The product is isolated by a process involving the addition of alcoholic solvent and filtration of the reaction mixture at 90-95° C.

The process described in WO 2006/027370 involves a lengthy process, the reaction proceeds at a high temperature i.e., above 125° C., it takes 19 hours for reaction completion, and also involves the hazard of filtration of a reaction mixture containing flammable solvents at 90-95° C. which poses problems in scale up operations. Based on the aforementioned drawbacks, this process may be unsuitable for preparation of the compound of formula I at laboratory scale and commercial scale operations.

A need remains for an improved and commercially viable process of preparing the compound of formula I or an acid addition salt thereof that will solve the problems associated with the processes described in the prior art, and that will be suitable for large-scale preparation. Desirable process properties include reduced reaction times, and greater simplicity, purity and yield of the product, thereby enabling the production of paliperidone and its pharmaceutically acceptable acid addition salts in high purity and in high yield.

SUMMARY

The present inventors have surprisingly found that paliperidone intermediate, 9-hydroxy-3-(2-chloroethyl)-2-methyl-4H-pyrido[1,2-a]pyrimidin-4-one, can be prepared in high purity and with high yield with a reduced reaction time by using phosphorous oxychloride as both a solvent and reactant in the reaction between 2-amino-3-hydroxypyridine and 2-acetylbutyrolactone instead of using reaction inert solvents like toluene. In one aspect, the process for the production of 9-hydroxy-3-(2-chloroethyl)-2-methyl-4H-pyrido[1,2-a]pyrimidin-4-one requires no reaction-inert solvent.

In an aspect, provided herein is an efficient, convenient and commercially viable process for the preparation of paliperidone intermediate, 9-hydroxy-3-(2-chloroethyl)-2-methyl-4H-pyrido[1,2-a]pyrimidin-4-one, and its hydrochloride salt. Advantageously, in the process described herein, no chromatographic separations are required for the isolation of pure 9-hydroxy-3-(2-chloroethyl)-2-methyl-4H-pyrido[1,2-a]pyrimidin-4-one, thereby making the process commercially viable.

DETAILED DESCRIPTION

In accordance with the present invention, there is provided an improved process for preparation of paliperidone intermediate, 9-hydroxy-3-(2-chloroethyl)-2-methyl-4H-pyrido[1,2-a]pyrimidin-4-one of formula I:

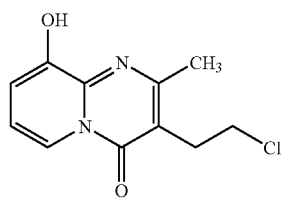

or its hydrochloride salt thereof which comprises:
a) reacting 2-amino-3-hydroxypyridine of formula II:

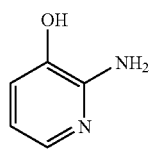

with 2-acetylbutyrolactone of formula III:

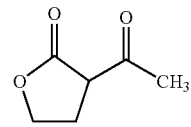

in the presence of phosphorous oxychloride to produce a reaction mass;
b) quenching the reaction mass in a mixture of ice and water to form a quenched reaction mass;
c) adjusting the pH of the quenched reaction mass to 4 - 6 with a base to produce a separated substantially pure compound of formula I;
d) collecting the separated substantially pure compound of formula I; and
e) optionally converting the compound of formula I into its substantially pure hydrochloride salt by reacting the separated substantially pure compound of formula I with an alcoholic or gaseous hydrogen chloride in a solvent selected from an alcoholic solvent and an aromatic solvent.

The reaction in step-(a) is carried out at a temperature of 20° C. to 70° C., specifically 25° C. to 70° C., and more specifically 25 to 60° C.

As used herein, "reaction-inert solvent" refers to a solvent which is inert to the reaction partners under the reaction conditions described herein, especially a solvent that is immiscible or only very poorly miscible with water, for example toluene, xylene, and the like.

In one embodiment, 1 to 2 equivalents of 2-acetylbutyrolactone of formula III per equivalent of 2-amino-3-hydroxypyridine of formula II are employed, specifically 1 to 1.3 equivalents of 2-acetylbutyrolactone per equivalent of the 2-amino-3-hydroxypyridine.

In one embodiment, 2.4 to 7 equivalents of phosphorous oxychloride per equivalent of 2-amino-3-hydroxypyridine of formula II are employed, specifically 3 to 6 equivalents of phosphorous oxychloride, and more specifically 3 to 4 equivalents of phosphorous oxychloride per equivalent of 2-amino-3-hydroxypyridine.

In another embodiment, the pH of the reaction mass in step-(c) is adjusted to 5-6.

The base used to adjust the pH in step-(c) is an organic or inorganic base. In one embodiment, the base is an aqueous solution of an inorganic base. Exemplary inorganic bases are aqueous ammonia; and hydroxides, carbonates, bicarbonates, alkoxides and oxides of alkali or alkaline earth metals. Exemplary alkali metal compounds are those of lithium, sodium and potassium, specifically those of sodium and potassium. Exemplary alkaline earth metal compounds are those of calcium and magnesium, specifically those of magnesium. Specific exemplary inorganic bases include aqueous ammonia, sodium hydroxide, potassium hydroxide, magnesium hydroxide, magnesium oxide, sodium carbonate, potassium carbonate, sodium bicarbonate, potassium bicarbonate, sodium tert-butoxide potassium tert-butoxide, and combinations comprising one or more of the foregoing inorganic bases. Specifically, the inorganic base is aqueous ammonia, sodium hydroxide, or potassium hydroxide, and more specifically aqueous ammonia.

The separated substantially pure compound of formula I in step-(d) is collected by filtration or centrifugation. The compound of formula I obtained is then optionally subjected to drying using conventional drying techniques like vacuum oven drying.

The compound of formula I obtained in step-(d) has a purity (measured by High Performance Liquid Chromatography, hereinafter referred to as 'HPLC') greater than about 97%, specifically greater than about 99%, and more specifically greater than about 99.5%.

The term "substantially pure compound of formula I or its hydrochloride salt" refers to the compound of formula I or its hydrochloride salt having purity greater than about 97%, specifically greater than about 99% and more specifically greater than about 99.5% (measured by HPLC).

Exemplary alcoholic solvents for use in step-(e) include methanol, ethanol, n-propanol, 2-propanol, n-butanol, tert-butanol, and combinations comprising one or more of the foregoing solvents. A specific alcoholic solvent is methanol.

Exemplary aromatic solvents for use in step-(e) are toluene, xylene, and the like, and combinations comprising one or more of the foregoing solvents. A specific aromatic solvent is toluene.

In one embodiment, the alcoholic hydrogen chloride used in step-(e) is methanolic hydrogen chloride.

In one embodiment, the purity (measured by HPLC) of the product obtained is greater than about 97%, specifically greater than about 99%, and more specifically greater than about 99.5%.

Paliperidone and pharmaceutically acceptable acid addition salts of paliperidone can be prepared in high purity by using the substantially pure compound of formula I or its hydrochloride salt obtained by the methods disclosed herein, by known methods, for example as described in U.S. Pat. No. 5,158,952.

HPLC Method Used in the Specification is Provided Below:

| | |
|---|---|
| Column: | Xterra - C18 or equivalent (150 mm × 4.6 mm, 5.0μ) |
| Mobile phase: | 20 mM phosphate buffer & methanol |
| Elution: | Gradient |
| Flow rate: | 1.0 ml/min |
| UV wave length: | 237 nm |
| Injection volume: | 20.0 μL |
| Total run time: | 35.0 min |
| Test solution: | 10.0 mg of 9-hydroxy-3-(2-chloroethyl)-2-methyl-4H-pyrido [1,2-a]pyrimidin-4-one in 10 ml volumetric flask and make up to the mark with diluent (Methanol:water (1:1)). |

The following examples are given for the purpose of illustrating the present invention and should not be considered as limitation on the scope or spirit of the invention.

EXAMPLES

Example 1

Preparation of 9-Hydroxy-3-(2-chloroethyl)-2-methyl-4H-pyrido[1,2-a]pyrimidin-4-one To a mixture comprising phosphorus oxychloride (2520 parts) and 2-amino-3-hydroxy pyridine (300 parts) was charged 2-acetyl butyrolactone (348 parts). The resulting mixture was heated to 60° to 65° C. and stirred for 10 hours at the same temperature. The reaction mass was cooled and poured into a mixture of ice and water to produce a quenched reaction mass. The pH was adjusted (pH meter) to 5.5 using aqueous ammonia. The resulting solid was filtered and washed with water followed by drying in vacuum oven to yield 235 parts of 9-hydroxy-3-(2-chloroethyl)-2-methyl-4H-pyrido[1,2-a]pyrimidin-4-one with a purity (HPLC) of 99%.

$^1$H-NMR (CDCl$_3$): δ 2.576 (3H,s), δ 3.189 (2H,t) δ 3.841 (2H,t), δ 4.3 (1H,bs), δ 7.022 (1H,m) δ 7.1 (1H,t) δ 8.46 (1H,d).

Example 2

Preparation of 9-hydroxy-3-(2-chloroethyl)-2-methyl-4H-pyrido[1,2-a]pyrimidin-4-one Hydrochloride 9-Hydroxy-3-(2-chloroethyl)-2-methyl-4H-pyrido[1,2-a]pyrimidin-4-one (235 parts) was added into methanol (1300 parts) which was then acidified and the pH was adjusted with 10-13% methanolic HCl (500 part) from 0-1. The reaction mass was concentrated into a thick slurry, filtered and washed with chilled methanol (100 parts). The product was dried at 60° C. under vacuum (700 mm Hg) to yield 219 parts of 9-Hydroxy-3-(2-chloroethyl)-2-methyl-4H-pyrido[1,2-a]pyrimidin-4-one with HPLC purity above 98%.

$^1$H-NMR (D$_2$O): δ2.414 (3H,s), δ 2.723 (2H,t) δ 3.904 (2H, t), δ 7.602 (1H, m), δ 7.747 (1H,d), δ 8.732 (1H,d).

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The term wt % refers to percent by weight. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A process for preparation of 9-hydroxy-3-(2-chloroethyl)-2-methyl-4H-pyrido[1,2-a]pyrimidin-4-one of formula I:

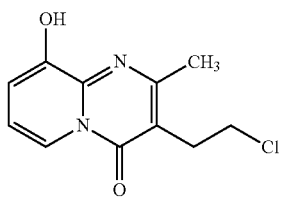

or its hydrochloride salt thereof comprising:
a) reacting 2-amino-3-hydroxypyridine of formula II:

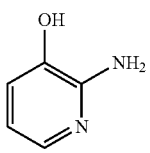

with 2-acetylbutyrolactone of formula III:

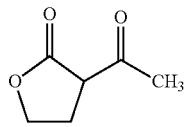

in the presence of phosphorous oxychloride to form a reaction mass;
b) quenching the reaction mass obtained in step-(a) in a mixture of ice and water to form a quenched reaction mass;
c) adjusting the pH of the quenched reaction mass to 4 - 6 with a base to produce a separated substantially pure compound of formula I;
d) collecting the separated substantially pure compound of formula I; and
e) optionally converting the separated substantially pure compound of formula I into its substantially pure hydrochloride salt by reacting the separated substantially pure compound of formula I with alcoholic or gaseous hydrogen chloride in a solvent selected from an alcoholic solvent and an aromatic solvent.

2. The process of claim 1, wherein the reaction in step-(a) is carried out at a temperature of 20° C. to 70° C.

3. The process of claim 1, wherein 1 to 2 equivalents of 2-acetylbutyro-lactone of formula III per equivalent of 2-amino-3-hydroxypyridine of formula II is used in step-(a).

4. The process of claim 3, wherein 1 to 1.3 equivalents of 2-acetylbutyro-lactone per equivalent of the 2-amino-3-hydroxypyridine is used.

5. The process of claim 1, wherein 2.4 to 7 equivalents of phosphorous oxychloride per equivalent of 2-amino-3-hydroxypyridine of formula II is used in step-(a).

6. The process of claim 5, wherein 3 to 4 equivalents of phosphorous oxychloride per equivalent of 2-amino-3-hydroxypyridine is used.

7. The process of claim 1, wherein the pH of the reaction mass in step-(c) is adjusted to 5 - 6; and wherein the base used is an organic or an inorganic base.

8. The process of claim 7, wherein the inorganic base is selected from the group consisting of aqueous ammonia, sodium hydroxide, potassium hydroxide, magnesium hydroxide, magnesium oxide, sodium carbonate, potassium carbonate, sodium bicarbonate, potassium bicarbonate, sodium tert-butoxide, potassium tert-butoxide, and combinations of the foregoing bases.

9. The process of claim 8, wherein the inorganic base is aqueous ammonia.

10. The process of claim 1, wherein the compound of formula I obtained in step-(d) has a purity of about 97% to about 99.5% as measured by HPLC.

11. The process of claim 1, wherein the alcoholic solvent used in step-(e) is selected from the group consisting of methanol, ethanol, n-propanol, 2-propanol, n-butanol, tert-butanol and combinations thereof; and wherein the aromatic solvent is selected from the group consisting of toluene, xylene and combinations thereof.

12. The process of claim 11, wherein the alcoholic solvent is methanol; and wherein the aromatic solvent is toluene.

13. The process of claim 1, wherein the alcoholic hydrogen chloride used in step-(e) is methanolic hydrogen chloride.

* * * * *